US012539370B1

(12) United States Patent
Nwaogbo

(10) Patent No.: US 12,539,370 B1
(45) Date of Patent: Feb. 3, 2026

(54) SMART SHARP OBJECT DISPOSAL HOUSING WITH LOAD-SENSING AND LOCKING MECHANISMS

(71) Applicant: Nelo LLC, Sparks, NV (US)

(72) Inventor: Chinelo Pearl Nwaogbo, Sparks, NV (US)

(73) Assignee: NELO LLC, Sparks, NV (US)

( * ) Notice: Subject to any disclaimer, the term of this patent is extended or adjusted under 35 U.S.C. 154(b) by 0 days.

(21) Appl. No.: 18/606,132

(22) Filed: Mar. 15, 2024

Related U.S. Application Data

(60) Provisional application No. 63/470,019, filed on May 31, 2023.

(51) Int. Cl.
*A61M 5/32* (2006.01)

(52) U.S. Cl.
CPC ... *A61M 5/3205* (2013.01); *A61M 2205/0238* (2013.01); *A61M 2205/18* (2013.01); *A61M 2205/3379* (2013.01); *A61M 2205/505* (2013.01); *A61M 2205/581* (2013.01); *A61M 2205/6063* (2013.01); *A61M 2209/06* (2013.01)

(58) Field of Classification Search
CPC ........ A61M 5/3205; A61M 2205/0238; A61M 2205/18; A61M 2205/3379; A61M 2205/505; A61M 2205/581; A61M 2205/6063; A61M 2209/06
USPC .......................................................... 206/366
See application file for complete search history.

(56) References Cited

U.S. PATENT DOCUMENTS

| | | | | |
|---|---|---|---|---|
| 5,046,614 | A | 9/1991 | Torres et al. | |
| 5,740,909 | A | 4/1998 | Nazare et al. | |
| 7,296,688 | B2 * | 11/2007 | Mallett | G06Q 40/08 206/366 |
| 7,660,724 | B2 * | 2/2010 | Mallett | A61B 50/36 206/366 |
| 8,573,426 | B2 * | 11/2013 | Maness | B09B 3/0075 206/370 |
| 8,616,397 | B2 * | 12/2013 | Maness | A61B 50/37 220/23.88 |
| 8,813,986 | B2 * | 8/2014 | Liscio | A61B 50/362 206/370 |

(Continued)

FOREIGN PATENT DOCUMENTS

| | | | |
|---|---|---|---|
| CA | 2112759 | C | 2/1997 |
| EP | 1001820 | B1 | 10/2004 |
| EP | 2358289 | B1 | 5/2014 |

*Primary Examiner* — Jacob K Ackun
(74) *Attorney, Agent, or Firm* — Torrey Pines Law Group PC

(57) ABSTRACT

The present invention relates to a sharp object disposal container designed for safe, reliable, and user-friendly disposal of used sharp objects. The container comprises a base, a lid, a plurality of sidewalls defining an interior space, a weighted plate within the base, a touch screen display on one of the sidewalls, and a tray suspended from the underside of the lid. The weighted plate detects the load of disposed sharp objects and triggers auditory alerts to indicate when the container is full. The tray tilts to drop sharp objects into the container and locks when the maximum load threshold is reached, preventing overfilling. This sharp object disposal container provides an improved solution for medical waste disposal in various settings, significantly reducing the risk of accidental needlestick injuries and contamination.

19 Claims, 14 Drawing Sheets

(56) References Cited

U.S. PATENT DOCUMENTS

| | | | |
|---|---|---|---|
| 9,796,526 B2 * | 10/2017 | Smith ........................ | B65F 1/10 |
| 10,335,244 B2 | 7/2019 | Norman et al. | |
| 10,869,731 B2 | 12/2020 | Norman et al. | |

* cited by examiner

SMART SHARP OBJECT DISPOSAL HOUSING WITH LOAD-SENSING AND LOCKING MECHANISMS

CROSS-REFERENCE TO RELATED APPLICATIONS

This application claims the benefit of U.S. Provisional Patent Application 63/470,019, filed on May 31, 2023, respectively, which is incorporated by reference herein in its entirety.

FIELD OF THE INVENTION

The present invention relates generally to the field of medical waste disposal, and more specifically, to a sharp object disposal container that safely and effectively manages the disposal of used sharp objects, while also providing features that notify users when the container is full and prevent overfilling.

BACKGROUND OF THE INVENTION

Medical waste, including used syringes, can pose a significant health risk to individuals exposed to it, as well as the environment. Syringes contaminated with bloodborne pathogens, such as hepatitis B, hepatitis C, and human immunodeficiency virus (HIV), can inadvertently transmit these diseases to individuals handling the waste, which can lead to serious health consequences. Additionally, improper disposal of used syringes can have detrimental effects on the environment, including pollution of water sources and the potential spread of diseases to wildlife.

In order to prevent these health risks and protect the public, syringes must be disposed of properly. Traditional syringe disposal containers typically include a rigid plastic or metal box with an opening through which the used syringes are inserted. However, these containers often lack a mechanism to indicate when they are full, which can result in overfilling and increased risk of exposure to contaminated syringes. Furthermore, traditional containers may not securely hold the syringes, increasing the possibility of accidental needlestick injuries during the disposal process.

Over the years, numerous attempts have been made to develop improved syringe disposal containers that address the various issues associated with traditional containers. Some of these designs include the following:

a) Sharps Containers with Fill-Level Indicators: Some containers have incorporated visual fill-level indicators, such as clear panels or markings on the sidewalls, to help users gauge the amount of space remaining in the container. While this design provides users with a visual cue to prevent overfilling, it may not be entirely accurate, as the syringes can be unevenly distributed within the container, leading to a false perception of the remaining capacity. Additionally, visual indicators may not be easily discernible in low-light conditions or when obscured by the contents of the container.

b) Containers with Mechanically-Activated Locking Systems: Other designs have incorporated mechanically-activated locking systems that automatically engage when the container reaches a certain level of fullness. These systems generally rely on the weight or volume of the disposed syringes to trigger the locking mechanism. While these designs may effectively prevent overfilling, they can be prone to mechanical failure or jamming, resulting in an unreliable and potentially unsafe disposal solution.

c) Electronic Monitoring Systems: Some containers have employed electronic monitoring systems to track the number or weight of syringes disposed of in the container. These systems typically use sensors, such as load cells or infrared sensors, to measure the disposed syringes and provide users with an indication of the remaining capacity. While electronic monitoring systems can offer a more accurate representation of the container's fullness, they can be more complex and expensive to implement, and may be subject to errors or malfunctions due to electrical or software issues.

d) Containers with Built-in Disinfection Mechanisms: In an effort to further reduce the risk of contamination and needlestick injuries, some containers have incorporated built-in disinfection mechanisms, such as ultraviolet (UV) light or chemical disinfectants, to sterilize the disposed syringes upon insertion. While these designs can provide an added layer of protection, they may not be entirely effective in neutralizing all pathogens and can increase the complexity and cost of the disposal container.

e) Syringe Disposal Containers with Bag Liners: Some containers have been designed to accommodate disposable bag liners that can be easily removed and replaced when the container is full. This design allows for more efficient and sanitary disposal of the used syringes. However, the reliance on bag liners can introduce additional problems, such as the risk of punctures or tears in the bag material, leading to potential contamination and exposure to hazardous waste.

f) Customizable and Modular Disposal Solutions: In order to accommodate varying needs and preferences, some syringe disposal container designs have incorporated customizable and modular features, such as adjustable size, shape, or capacity. These designs allow users to tailor the container to their specific requirements and preferences. However, the complexity and variability of these designs may increase the likelihood of user error or misuse, which can compromise the safety and effectiveness of the disposal system.

Despite these various attempts to improve upon traditional syringe disposal container designs, many existing solutions still suffer from a range of shortcomings. For instance, some designs may not provide adequate safety measures to prevent accidental needlestick injuries or contamination, while others may lack user-friendly features that promote proper use and maintenance. Additionally, some designs may be more prone to mechanical or electrical failure, rendering them unreliable or potentially unsafe.

In light of these limitations, there remains a significant need for an improved syringe disposal container that effectively addresses the aforementioned issues, providing a safe, reliable, and user-friendly solution for the disposal of used syringes while minimizing the risk of accidental needlestick injuries and contamination. The ideal syringe disposal container would incorporate features that not only notify users when the container is full, but also lock the container to prevent overfilling, enable easy removal and replacement of the waste bag, and ensure proper disposal of syringes to mitigate potential hazards.

SUMMARY OF THE INVENTION

The present invention is a sharp object disposal housing that offers a safe, reliable, and user-friendly solution for disposing of used sharp objects. The housing comprises a base, a lid, a plurality of sidewalls defining an interior space, a weighted plate within the base, a touch screen display on one of the sidewalls, a tray suspended from the underside of the lid, and optionally, a removable mount, a speaker, and a bag. The unique features of the housing include a locking mechanism that prevents overfilling, a tray that tilts and drops the sharp objects into the housing, a touch screen display that provides housing status and user settings, and additional optional features like a removable mount, a speaker, and a bag for easy disposal.

The benefits of the present invention over prior art are numerous. By incorporating features that notify users when the housing is full and lock the housing to prevent overfilling, the invention significantly minimizes the risk of accidental needlestick injuries and contamination. The user-friendly design, including the tilting tray and touch screen display, enhances the overall experience and ensures proper disposal of sharp objects. Additionally, the optional features, such as the removable mount and speaker, further contribute to the housing's safety and convenience. The present invention is a significant improvement over prior art, making it an ideal solution for medical waste disposal in various settings, such as hospitals, clinics, laboratories, and other facilities that handle sharp objects and other sharps.

In a first implementation of the invention, a sharp object disposal housing comprises:

- a base, a lid, and a plurality of sidewalls defining an interior space for disposing used sharp objects;
- a weighted plate located within the base and in electronic communication with a touch screen display positioned on one of the plurality of sidewalls, wherein the weighted plate is configured to detect a maximum load threshold of disposed sharp objects and cause the touch screen display to indicate that the housing is full upon reaching the maximum load threshold; and
- a tray suspended from an underside of the lid and extending into the interior space, configured to receive a sharp object for disposal and tilt to release the sharp object onto the weighted plate within the interior space, wherein the tray further comprises a locking mechanism that engages when the maximum load threshold is reached, preventing further insertion of sharp objects.

In a second aspect, the sharp object disposal housing may further comprise a removable mount positioned on at least one of the plurality of sidewalls, the removable mount being spring-loaded.

In another aspect, the removable mount may be releasable through a key mechanism located on an opposite sidewall.

In another aspect, the sharp object disposal housing may further comprise a speaker mounted on at least one of the plurality of sidewalls, wherein the speaker is configured to audibly announce that the housing is full when the maximum load threshold is reached.

In another aspect, the sharp object disposal housing may further comprise a bag disposed within the interior space.

In another aspect, wherein upon removal of the bag when the maximum load threshold is reached and replacement with a new empty bag, the weighted plate resets and the tray returns to an original configuration to accept additional sharp objects for disposal.

In another aspect, the touch screen display may provide visual alerts indicating the remaining capacity of the housing.

In another aspect, the touch screen display may provide instructions for proper use and maintenance of the housing.

In another aspect, the tray may include a safety barrier to prevent accidental contact with disposed sharp objects.

In another aspect, the plurality of sidewalls may be made of a puncture-resistant material.

In another aspect, the base, lid, and plurality of sidewalls are made of a material that is resistant to chemical corrosion.

In another aspect, the interior space is configured to accommodate disposable bag liners.

In another aspect, the sharp object disposal housing may further comprise a bag liner retaining mechanism for securing disposable bag liners within the interior space.

In another aspect, the maximum load threshold may be adjustable based on user preferences or regulatory requirements.

In another aspect, the sharp object disposal housing may further comprise an electronic communication module for transmitting housing status information to a remote device.

In another aspect, the sharp object disposal housing may further comprise a disinfection mechanism for sterilizing the disposed sharp objects.

In another aspect, the disinfection mechanism may comprise an ultraviolet (UV) light source.

In another aspect, the disinfection mechanism may comprise a chemical disinfectant.

In another aspect, the locking mechanism may be automatically disengaged upon removal of the disposed sharp objects and resetting of the weighted plate.

In another aspect, the sharp object disposal housing may further comprise a handle on the lid for facilitating transportation and disposal of the housing.

In another implementation of the present invention, a sharp object disposal housing comprises: a base, a lid, and a plurality of sidewalls defining an interior space for disposing used sharp objects, the plurality of side walls including a front housing and a back housing that are removable from each other, wherein the lid acts as a front facing door; a container within the housing configured to accept the disposed used sharp objects and accessible through the front facing door; a sensing mechanism located within the base and in electronic communication with a tray configured to accept the disposed used sharp objects, wherein the sensing mechanism is configured to detect a maximum load threshold of disposed sharp objects within the container within the housing; a touch screen display integrated into the front housing for real-time load information; a speaker system in a lower assembly affixed to both the front housing and the back housing for auditory alerts at maximum load; and wherein the tray is suspended from an underside of the lid and extending into the interior space, configured to receive a sharp object for disposal and tilt to release the sharp object onto the base within the interior space, wherein the tray further comprises a locking mechanism that engages when the maximum load threshold is reached, preventing further insertion of sharp objects.

In another implementation of the present invention, a method for disposing used sharp objects using a sharp object disposal housing, the method comprises the steps of:

- providing a sharp object disposal housing, wherein the housing comprises a base, a lid, a plurality of sidewalls defining an interior space, a weighted plate located within the base and in electronic communication with a touch screen display positioned on one of the plurality of sidewalls, and a tray suspended from an underside of the lid and extending into the interior space;
- placing a sharp object to be disposed onto the tray;
- tilting the tray to release the sharp object onto the weighted plate within the interior space;
- detecting the weight of the disposed sharp object by the weighted plate;
- updating the touch screen display with the current load of disposed sharp objects;

determining whether the maximum load threshold of disposed sharp objects has been reached based on the weight detected by the weighted plate;

locking the tray in a tilted position when the maximum load threshold is reached to prevent further insertion of sharp objects; and unlocking the tray and resetting the weighted plate upon removal of the disposed sharp objects from the interior space to allow for additional sharp object disposal.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

Figure 1:
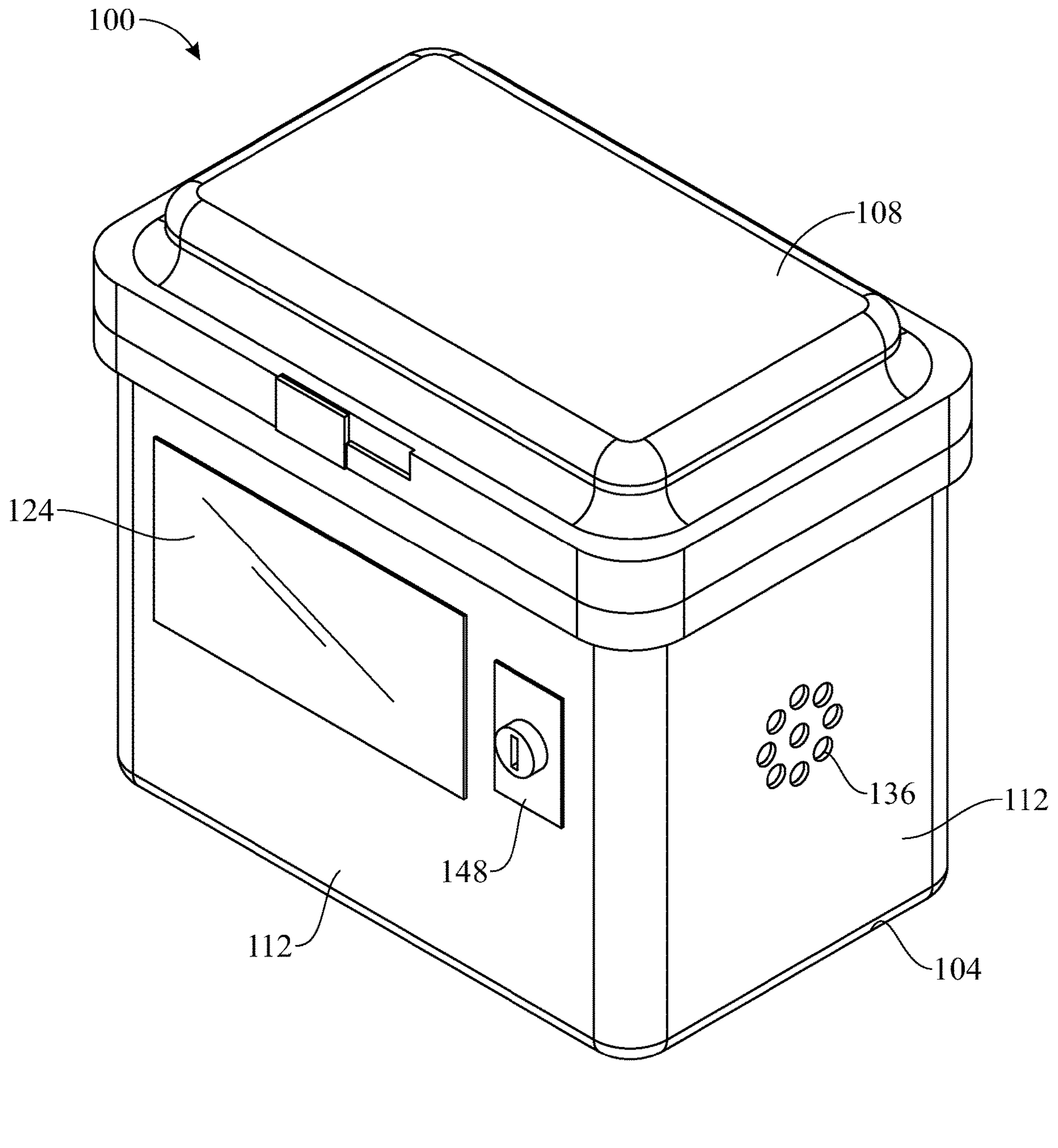
FIG. 1 presents a front perspective view of a sharp object disposal housing, in accordance with a first illustrative embodiment of the invention.
Figure 2:
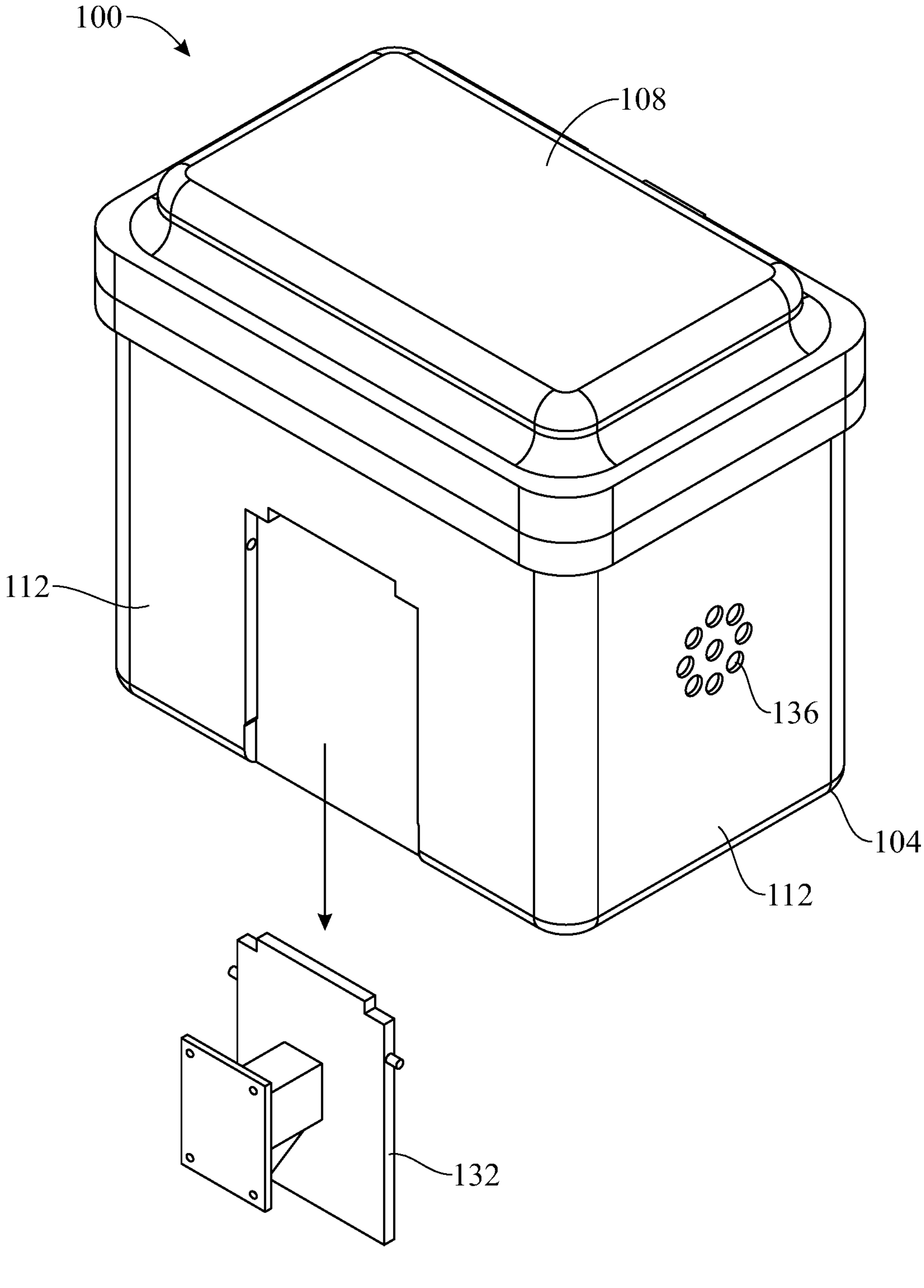
FIG. 2 presents a rear perspective view of the sharp object disposal housing illustrated in FIG. 1, shown with the housing being placed onto a releasable mount.
Figure 3:
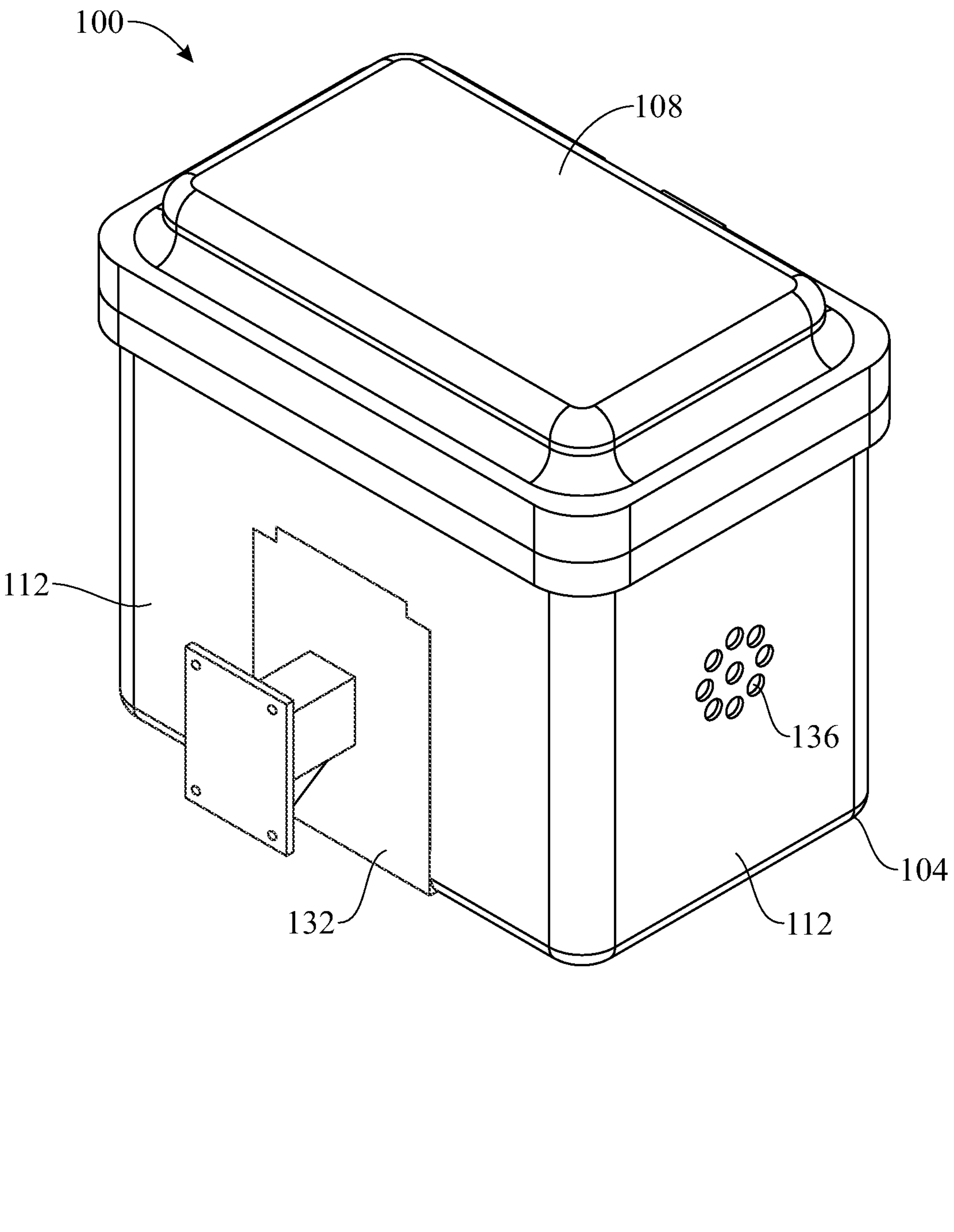
FIG. 3 presents a rear perspective view of the sharp object disposal housing illustrated in FIG. 2, shown after being placed onto the releasable mount.
Figure 4:
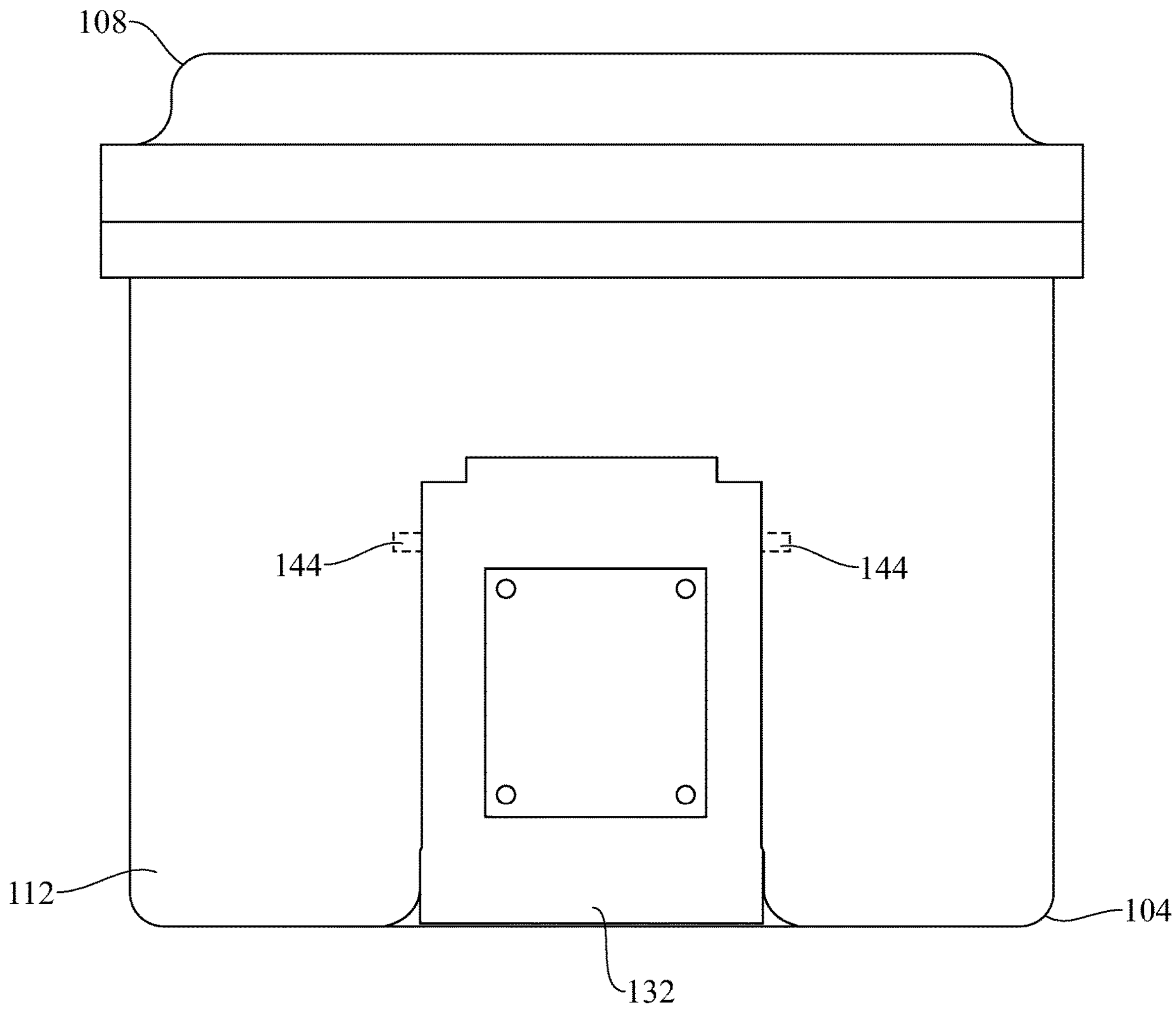
FIG. 4 presents a rear view of the sharp object disposal housing illustrated in FIG. 3.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention provides a novel sharp object disposal housing that addresses the limitations of prior art by offering a safe, reliable, and user-friendly solution for disposing of used sharp objects. The sharp object disposal housing 100 comprises a base 104, a lid 108, a plurality of sidewalls 112 defining an interior space 116, a weighted plate 120 within the base 104, a touch screen display 124 on one of the sidewalls 112, a tray 128 suspended from the underside of the lid 108, and optionally, a removable mount 132, a speaker 136, and a bag.

Referring initially to FIG. 1, the base 104 of the sharp object disposal housing 100 serves as a stable foundation for the housing 100 and supports the plurality of sidewalls 112 and the lid 108. The base 104 may have a flat, non-slip surface to ensure that the housing 100 remains securely in place during use. The base 104 may be constructed from a durable, puncture-resistant material that is resistant to chemical corrosion and easy to clean. The base 104 may also have a reinforced structure to support the weight of disposed sharp objects and other components of the housing 100.

The plurality of sidewalls 112 and the lid 108 create the enclosure that defines the interior space 116 of the sharp object disposal housing 100. The sidewalls 112 may be of various shapes and sizes, depending on the desired capacity and configuration of the housing 100. The sidewalls 112 may be made from a puncture-resistant material that is resistant to chemical corrosion and easy to clean. The sidewalls 112 may also include various components, such as the touch screen display 124, the speaker 136, the removable mount 132, and other optional features. The sidewalls 112 may be designed with a double-wall construction, providing additional protection against punctures and leaks.

Figure 5:
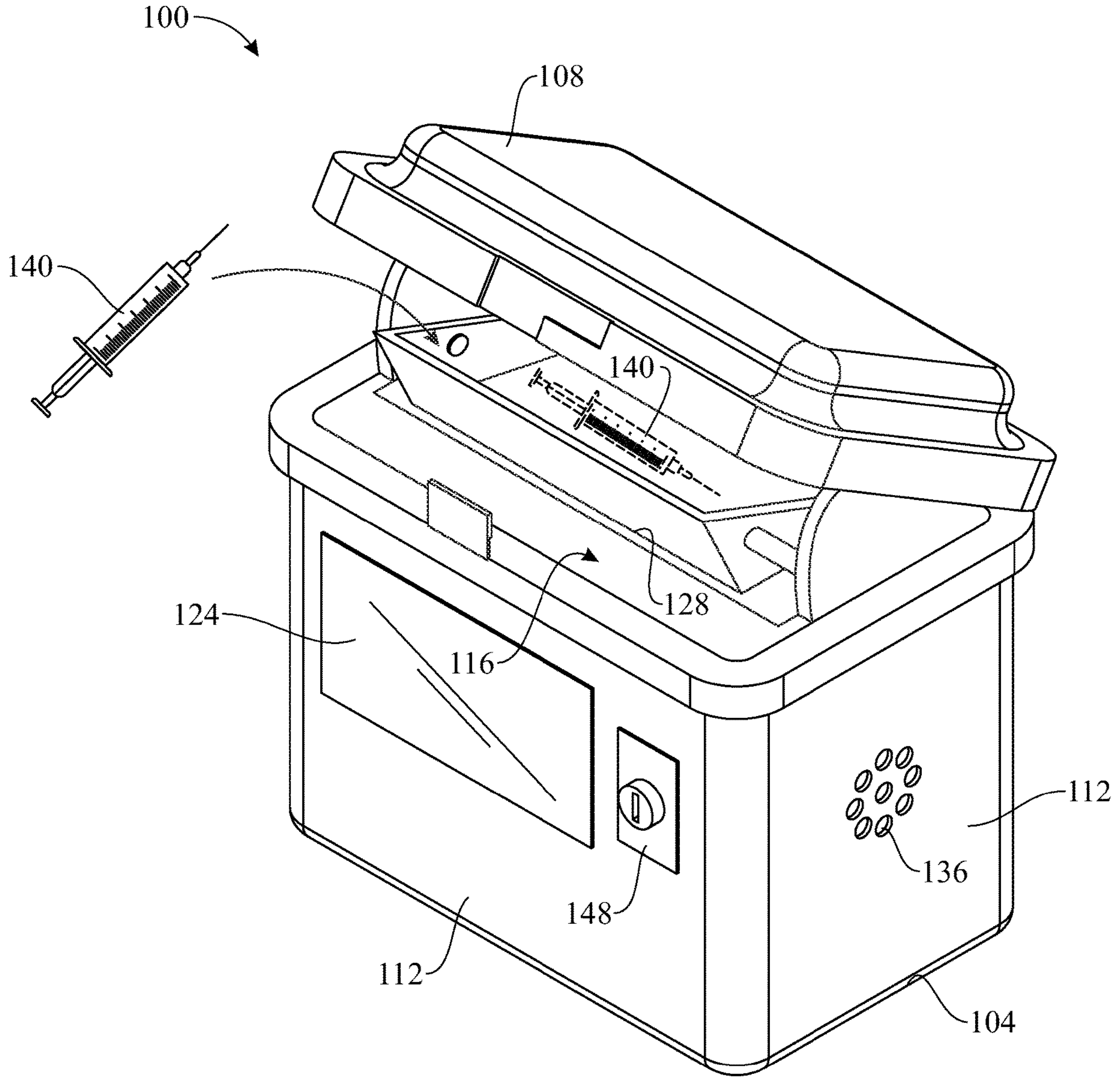
FIG. 5 presents a front perspective view of the sharp object disposal housing illustrated in FIG. 1, shown with the housing open and a sharp object being placed onto a tray hanging from an underside of the lid of the housing.
Figure 6:
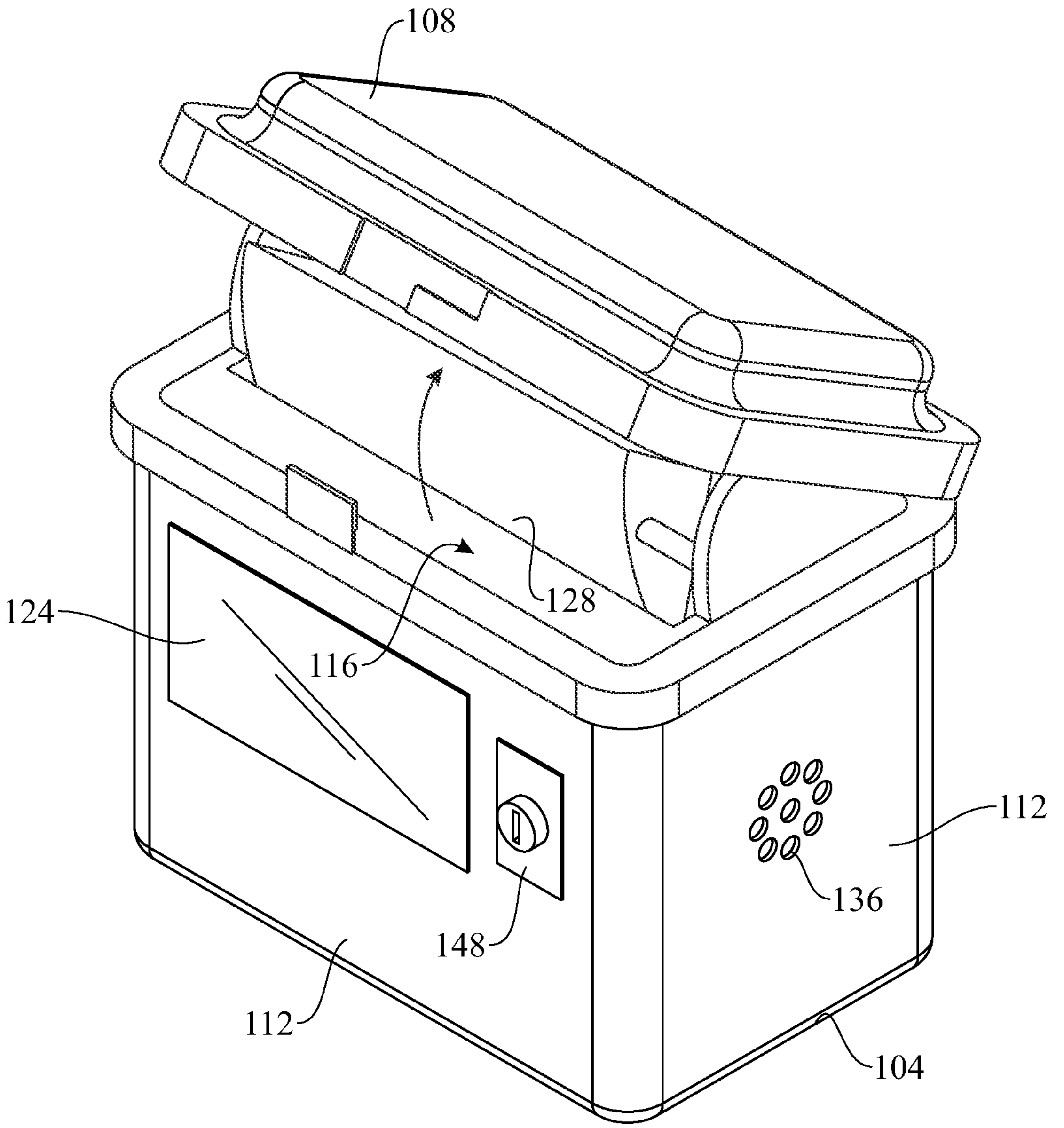
FIG. 6 presents a front perspective view of the sharp object disposal housing illustrated in FIG. 5, shown with the tray tilted to release the sharp object into an interior space of the housing.

Referring now to FIGS. 5-6, the lid 108 of the sharp object disposal housing 100 serves to close and seal the housing 100, preventing access to the disposed sharp objects and reducing the risk of accidental needlestick injuries. The lid 108 may be hinged, allowing for easy opening and closing of the housing 100 during use and maintenance. The lid 108 may also include a locking mechanism to secure the housing when it is not in use or when it is full, further enhancing the safety of the disposal process. The lid 108 may be constructed from a durable, puncture-resistant material that is resistant to chemical corrosion and easy to clean.

Figure 7:
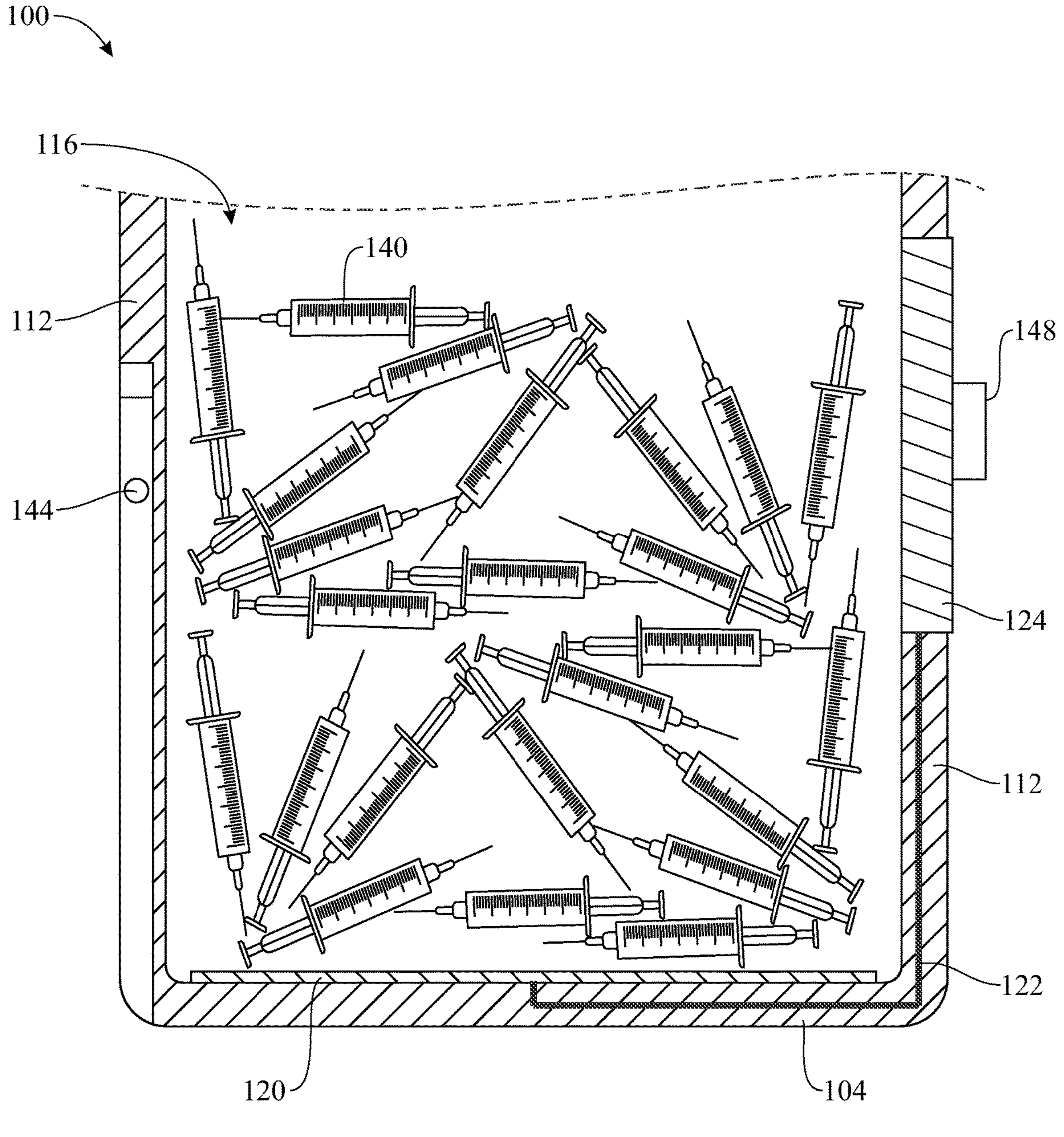
FIG. 7 presents a front perspective, cross-sectional view of the sharp object disposal housing illustrated in FIG. 1, shown with the interior space of the housing filled with disposed sharp objects.

Referring now to FIG. 7, the weighted plate 120, located within the base of the housing 100, is a crucial component of the present invention. It serves to detect the weight of disposed sharp objects and determine when the maximum load threshold has been reached. The weighted plate 120 may be constructed from a durable material that is resistant to chemical corrosion and easy to clean. The plate 120 may be designed to accommodate various types and sizes of sharp objects 140 and may be calibrated to accurately detect the weight of the disposed sharp objects 140. The weighted plate 120 may also include sensors for detecting the presence of a bag within the housing and other components that may affect the weight of the disposed sharp objects 140.

Figure 8:
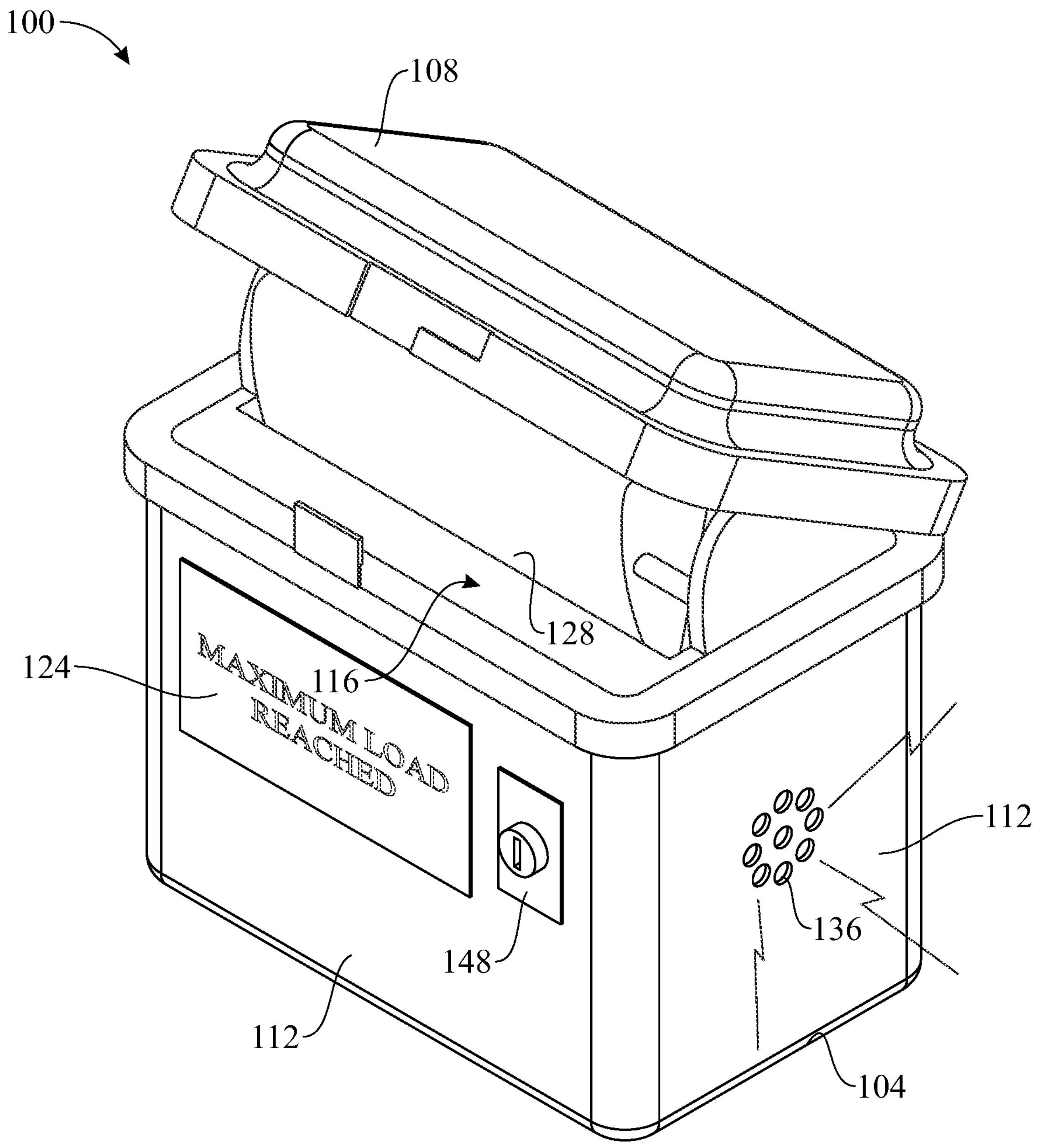
FIG. 8 presents a front perspective view of the sharp object disposal housing illustrated in FIG. 1, shown when the housing has reached maximum load capacity.
Figure 9:
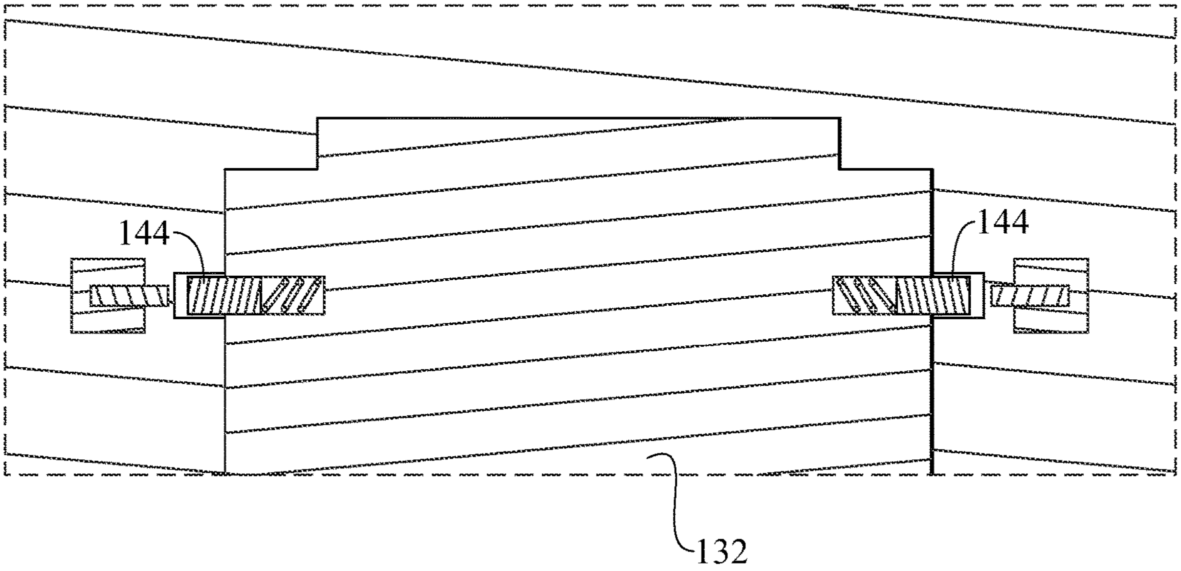
FIG. 9 presents a rear, cross-sectional view of the sharp object disposal housing illustrated in FIG. 4, shown with the removable mount locked into the housing.
Figure 10:
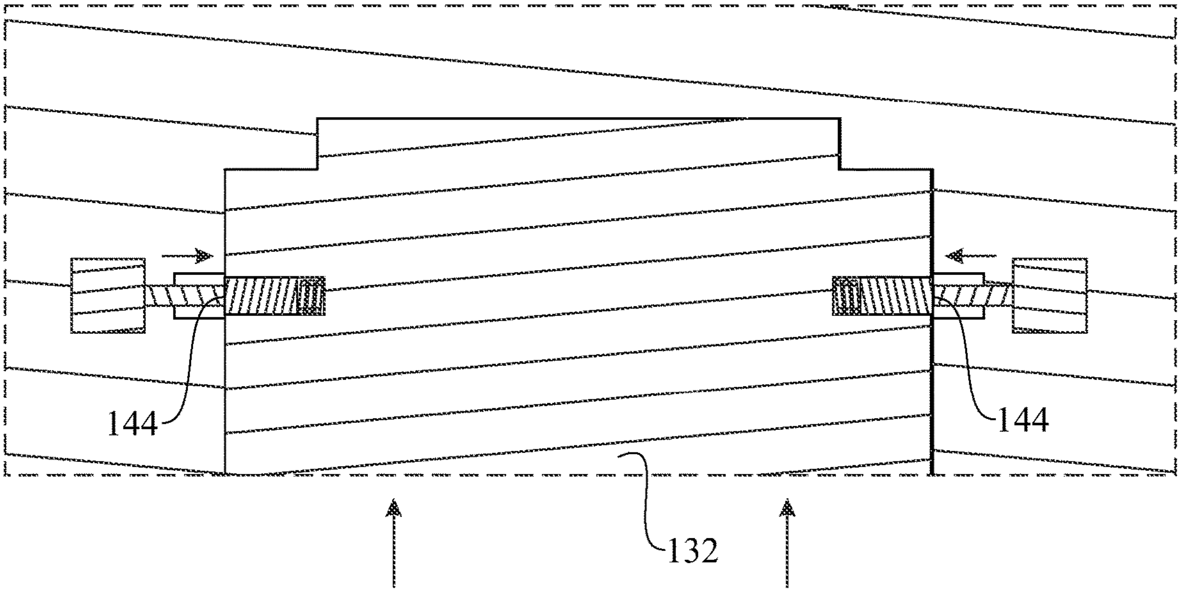
FIG. 10 presents a rear, cross-sectional view of the sharp object disposal housing illustrated in FIG. 4, shown with a sides of the removable mount being spring loaded such that the mount may be removed from the housing.
Figure 11:
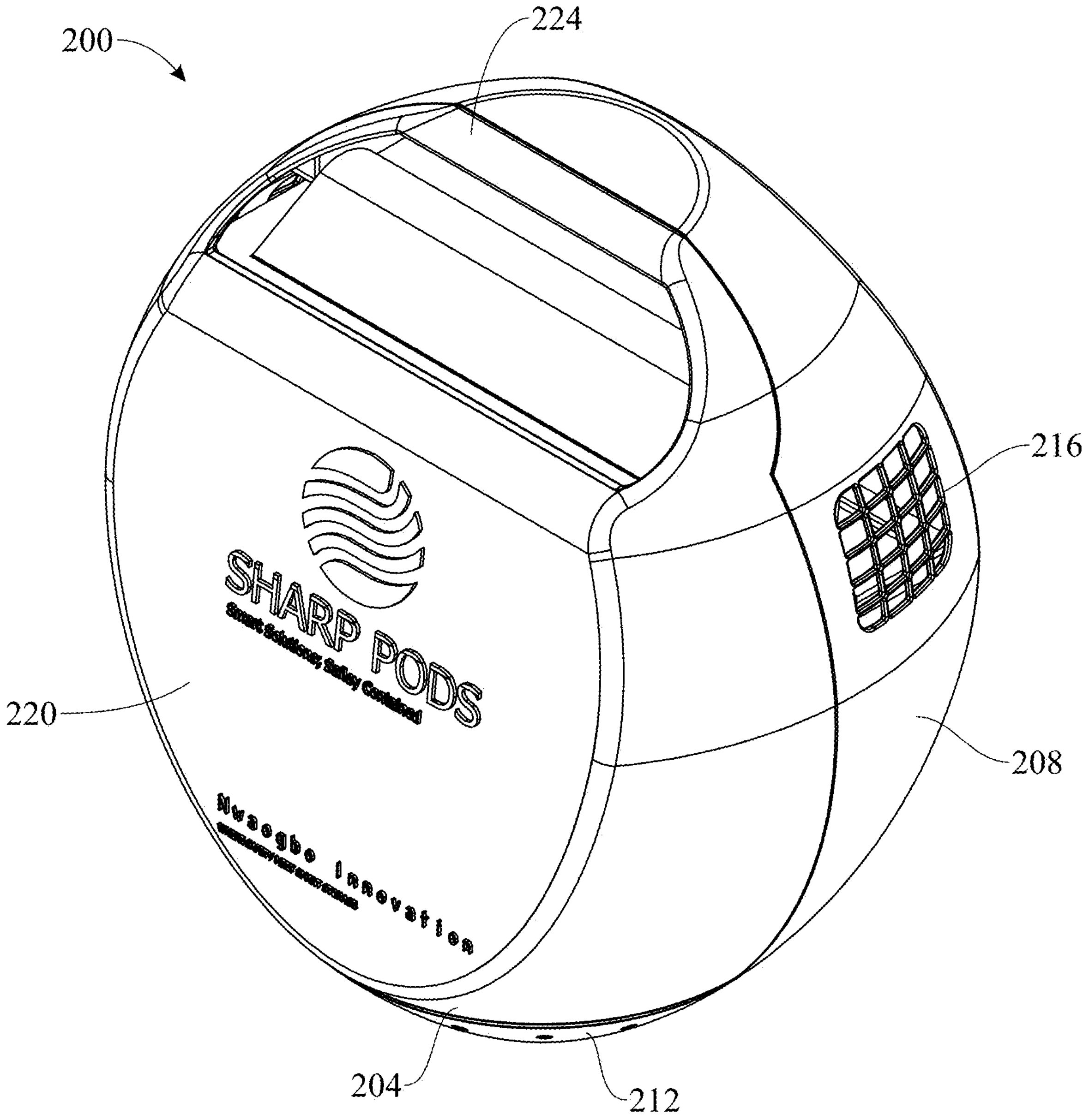
FIG. 11 presents a front perspective view of a sharp object disposal housing, showing the front housing and front door in a closed position, in a second illustrative embodiment of the present invention.
Figure 12:
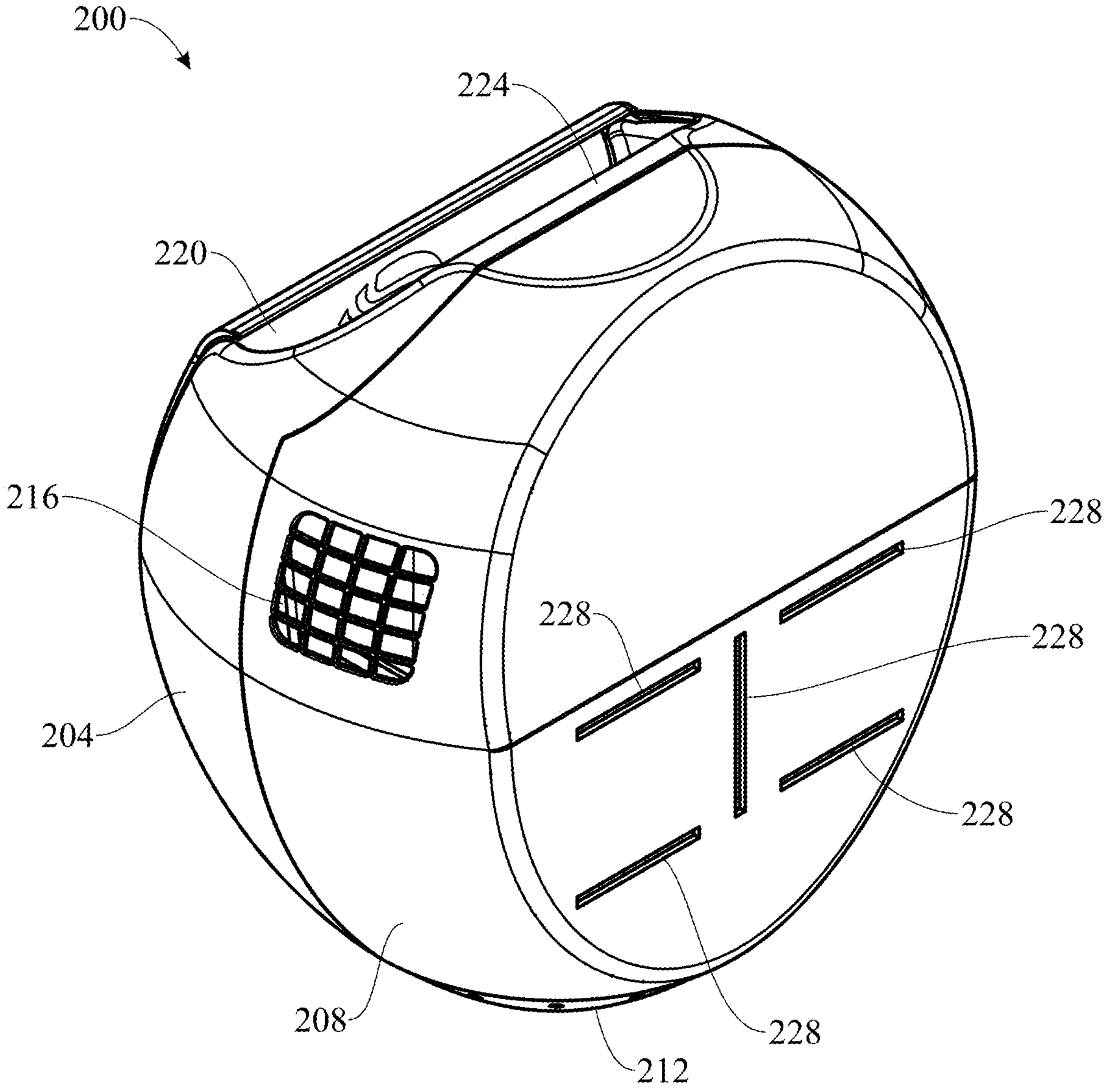
FIG. 12 presents a rear perspective view of the sharp object disposal housing, highlighting the back housing and the lower assembly/speaker.
Figure 13:
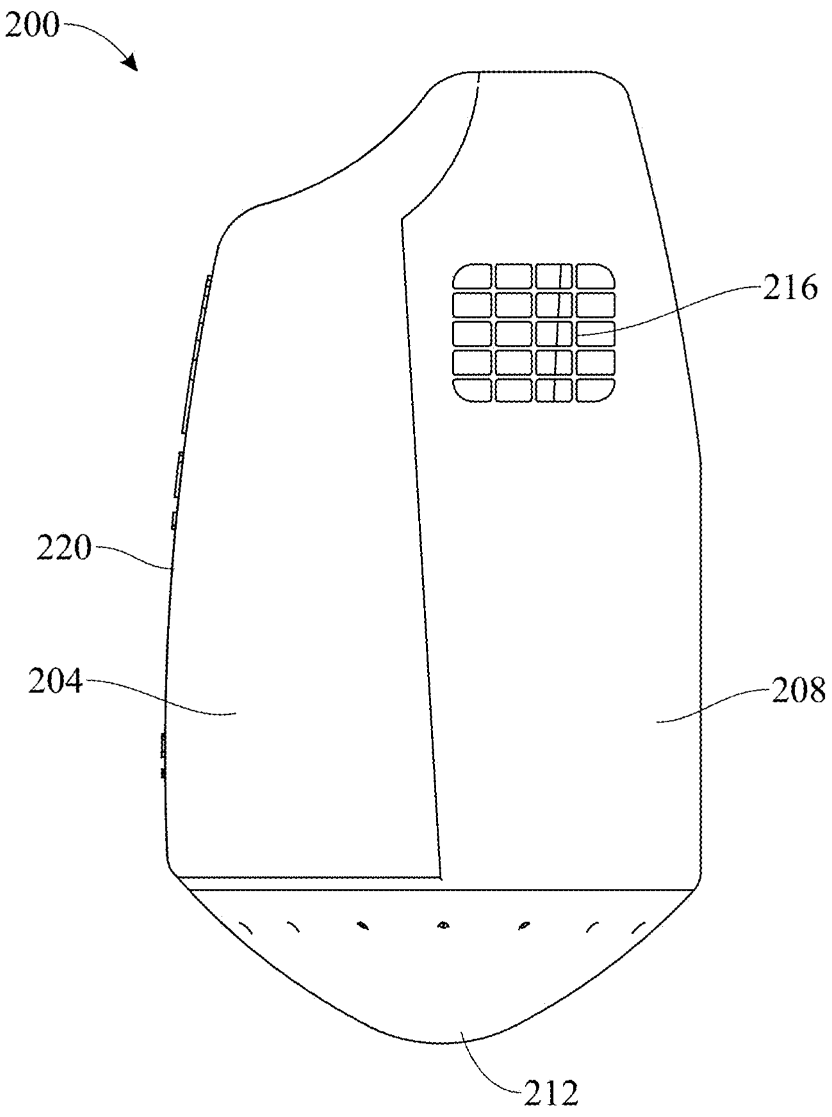
FIG. 13 presents a side perspective view of the sharp object disposal housing, showing the side profile with the front door attached to the front housing and the handle.
Figure 14:
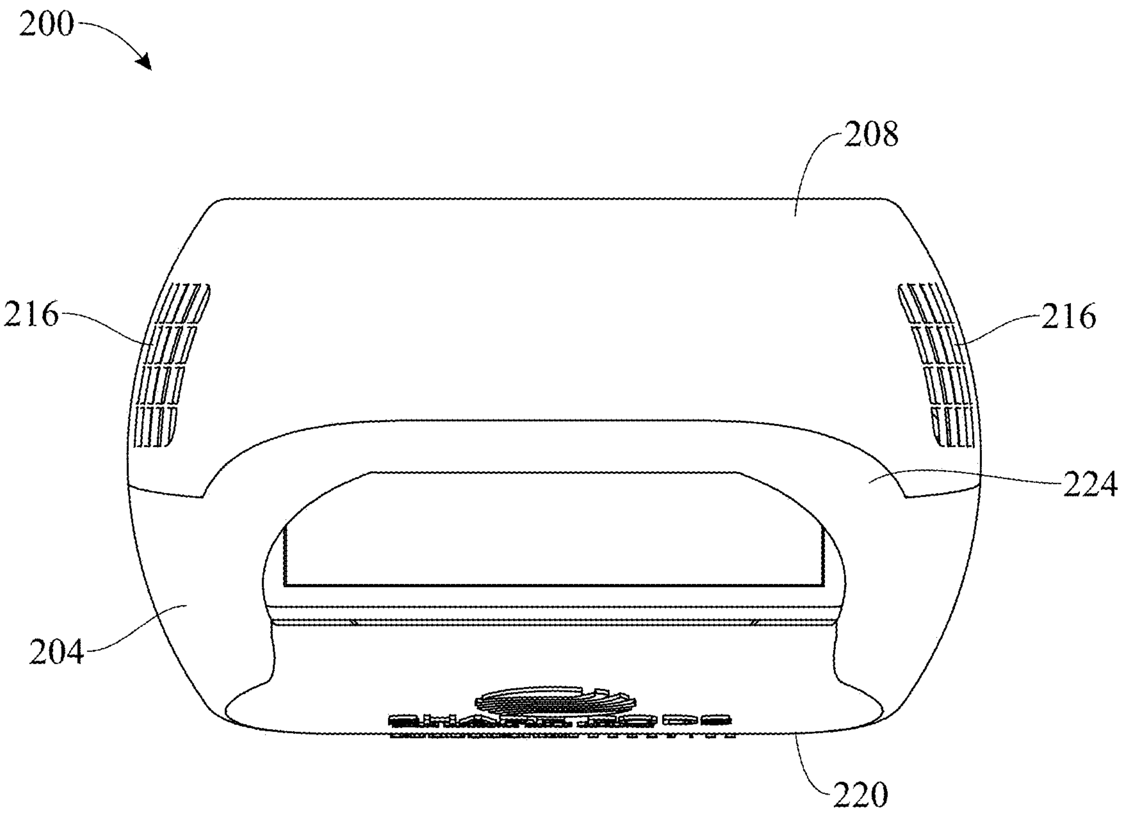
FIG. 14 presents a front perspective view of the sharp object disposal housing, with the front door open to reveal the interior space of the container and the tray.
Figure 15:
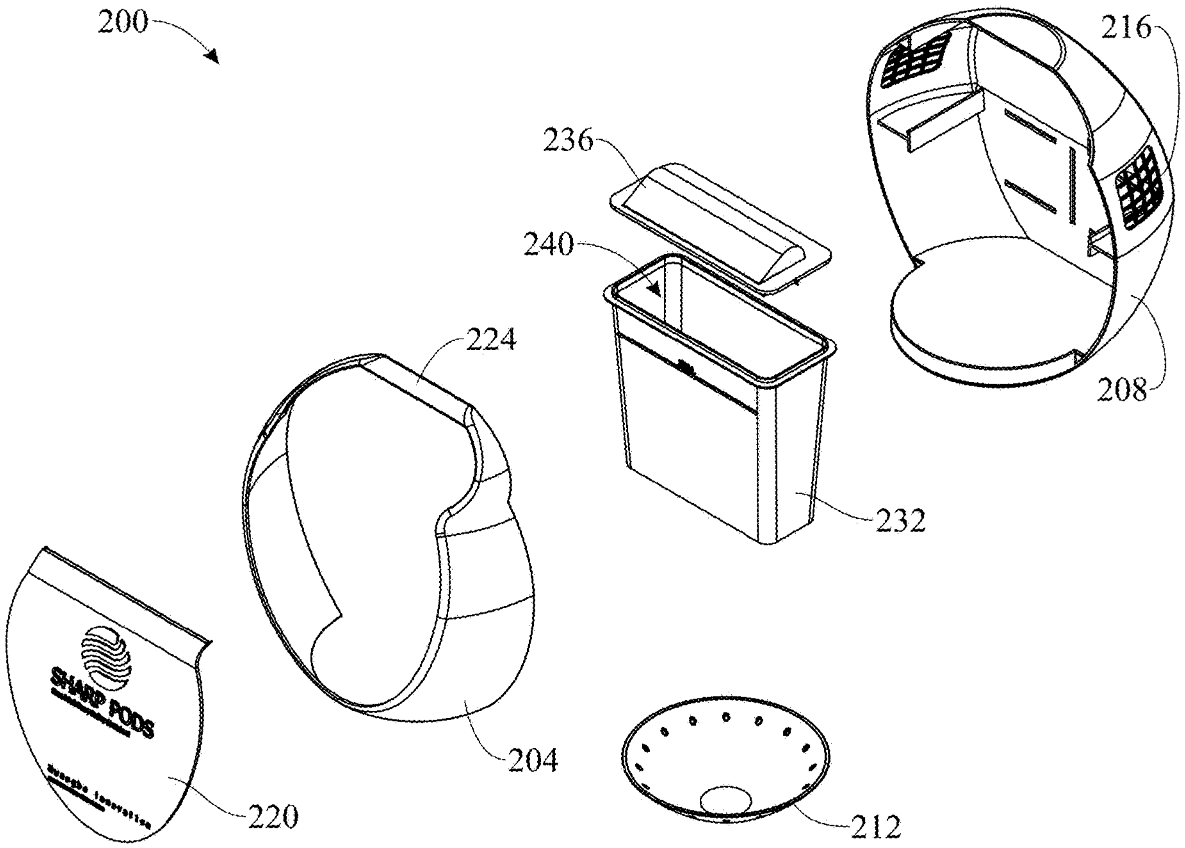
FIG. 15 presents an exploded view of the sharp object disposal housing, focusing on the mounting slits located on the back housing for secure attachment of the housing.

Referring now to FIG. 8, the touch screen display 124, positioned on one of the plurality of sidewalls 112, provides a user interface for accessing information about the housing 100 and its contents. The touch screen display 124 may be a high-resolution, full-color display that is easy to read and navigate. The display 124 may be in electronic communication 122 with the weighted plate 120 and may provide information about the remaining capacity of the housing 100, as best shown in FIGS. 7 and 8. The touch screen display 124 may also update the status of the locking mechanism, instructions for use and maintenance, and other relevant information. The touch screen display may also include customizable settings, allowing users to adjust the maximum load threshold, notification preferences, and other parameters.

Referring back to FIGS. 5-6, the tray 128, suspended from the underside of the lid 108 and extending into the interior space 116 of the housing 100, serves as a convenient and safe mechanism for disposing of used sharp objects. The tray 128 may be designed to accommodate various types and sizes of sharp objects and may include a non-slip surface to ensure that the sharp objects remain securely in place during disposal. The tray 128 may also include a safety barrier, such as a raised edge or a partial enclosure, to prevent accidental contact with disposed sharp objects 140. The tray 128 may be constructed from a durable, puncture-resistant material that is resistant to chemical corrosion and easy to clean. The tray 128 may also be detachable from the lid 108 for easy cleaning, maintenance, and replacement if necessary.

Referring now to FIGS. 2-4, and FIGS. 9-10 the removable mount 132, which may be positioned on at least one of the plurality of sidewalls 112, can provide a secure mounting point for the sharp object disposal housing 100. The mount 132 can be spring-loaded 144 and may be released through a key mechanism 148, as best shown in FIG. 1, located on an opposite sidewall 112. This feature allows the housing 100 to be easily removed from the mount 132 for cleaning, maintenance, and disposal of the waste bag. The removable mount 132 may be constructed from a durable material that is resistant to chemical corrosion and able to support the weight of the housing 100 and its contents.

Referring back to FIG. 8, the speaker 136, mounted on at least one of the plurality of sidewalls 112, serves to audibly announce when the housing 100 is full, providing an additional layer of safety and convenience for users. The speaker 136 may be configured to emit a loud, clear signal that is easily heard in noisy environments, such as hospitals and laboratories. The speaker 136 may also be adjustable, allowing users to control the volume and tone of the audible alerts. In some embodiments, the speaker 136 may provide verbal instructions for use and maintenance of the housing 100, further enhancing the user experience.

The bag, which may be placed within the housing 100, serves to contain the disposed sharp objects and facilitate easy removal and disposal of the waste. The bag may be made from a puncture-resistant material, such as heavy-duty plastic or reinforced fabric, to ensure the safe containment of used sharp objects. The bag may include a drawstring or other closure mechanism to securely seal the bag during removal and disposal. In some embodiments, the bag may include an identification label or tag for tracking and documentation purposes.

In a second embodiment of the sharp object disposal housing 200, the design prioritizes user safety and convenience with a modular approach. This embodiment, illustrated in FIGS. 11-15, features a robust front housing 204 and a sturdy back housing 208, providing a durable structure that can withstand regular use in various environments.

A significant innovation in this design is the incorporation of a mesh screen 216, which replaces the interactive display of the first embodiment. This screen allows users to visually monitor the fill level of the container 232 inside the housing, enhancing the ability to manage waste effectively. The visibility provided by this screen is crucial for maintaining safety standards and preventing overfilling.

The front door 220, seamlessly integrated into the front housing 204, offers easy access to the interior space 240. This design consideration simplifies the process of disposing of sharp objects, making it safer and more efficient. The door's design also ensures that it can be securely closed, thereby containing the sharp objects and reducing the risk of accidental exposure.

Furthermore, the housing includes a lower assembly with a built-in speaker system 212. This feature provides audible alerts or instructions, which is particularly useful in busy or noisy environments where visual cues might be missed.

Portability and ease of installation are also key considerations in this design. The handle 224 on the front housing ensures that the unit can be easily moved or transported as needed, catering to the dynamic requirements of different medical settings. Additionally, mounting slits 228 located on the housing enable secure and straightforward installation in various locations, providing flexibility in how and where the unit can be used.

Inside, the container 232 and tray 236 are meticulously designed for the efficient and hygienic disposal of sharp objects. The interior space 240 is sized to accommodate a substantial volume of waste, making the unit highly practical for areas with high usage. This careful consideration of capacity and functionality ensures that the disposal process is not only safe but also convenient for users.

Overall, this second embodiment of the sharp object disposal housing showcases a thoughtful approach to design, focusing on ease of use, safety, and adaptability in diverse medical environments. The features and modifications introduced in this version make it a versatile and user-friendly solution for the disposal of sharp objects in healthcare and other settings.

In some embodiments, the sharp object disposal housing may include additional safety features, such as a tamper-evident seal, to ensure that the housing remains secure and uncompromised during use and disposal. The seal may be positioned on the lid, the sidewalls, or other components of the housing and may be designed to provide visual or audible evidence of tampering. The tamper-evident seal may be constructed from a durable material that is resistant to chemical corrosion and difficult to remove or bypass.

Another optional feature of the sharp object disposal housing is an integrated barcode scanner, which can be positioned on one of the plurality of sidewalls or incorporated into the touch screen display. The barcode scanner can be used to scan the barcodes on sharp objects or other medical sharps before disposal, providing a convenient method for tracking and documenting the disposal of medical waste. The barcode scanner may be compatible with various barcode formats and may be configured to store scanned information locally or transmit it to a remote device for further processing.

In certain embodiments, the sharp object disposal housing may include a ventilation system to prevent the build-up of unpleasant odors within the housing. The ventilation system may include vents, filters, or other components that allow for the exchange of air between the interior and exterior of the housing while maintaining the security and integrity of the disposed sharp objects. The ventilation system may be designed to minimize the risk of contamination and the spread of infectious diseases.

In alternative embodiments of the present invention, the sharp object disposal housing may incorporate different features and designs to cater to specific user requirements or preferences. For instance, the housing may be designed in various shapes, sizes, and capacities to accommodate different volumes of sharp object waste, depending on the specific needs of a particular facility. The locking mechanism may be enhanced with biometric authentication or RFID tags, such as fingerprint or facial recognition, to further secure the housing and restrict access to authorized personnel only. The touch screen display may be replaced with an alternative user interface, such as a series of physical buttons, a voice-activated system, or a mobile application for remote monitoring and control. Additionally, the housing could include an ultraviolet (UV) light or other sterilization systems to disinfect disposed sharp objects and reduce the risk of contamination. The variety of alternative embodiments allows for customization and adaptation of the sharp object disposal housing to meet the diverse needs of different medical settings and users.

The present invention provides a sharp object disposal housing that effectively addresses the limitations of prior art by offering a safe, reliable, and user-friendly solution for the disposal of used sharp objects. By incorporating features that not only notify users when the housing is full but also lock the housing to prevent overfilling, enable easy removal and replacement of the waste bag, and ensure proper disposal of sharp objects, the present invention significantly minimizes the risk of accidental needlestick injuries and contamination. The unique combination of features provided by the present invention makes it an ideal solution for medical waste disposal in various settings, such as hospitals, clinics, laboratories, and other facilities that handle sharp objects and other sharps. The present invention streamlines the disposal process, making it more efficient and reducing the amount of time and effort required by healthcare workers and waste management personnel. The housing's durable construction and puncture-resistant materials ensure long-lasting performance, even in high-traffic environments with frequent use. The integration of technology, such as the touch screen display and electronic communication modules, enables remote monitoring and management of housing capacity, further contributing to efficient and effective medical waste disposal. Overall, the present invention provides a comprehensive solution that addresses the needs and concerns of various stakeholders in the medical waste disposal process, including healthcare providers, waste management personnel, and regulatory agencies.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A sharp object disposal system comprising:

a base, a lid, and a plurality of sidewalls defining an interior space configured to receive used sharp objects;

a container associated with the housing and configured to accumulate the used sharp objects;

a sensing mechanism located within the base and in electronic communication with a control unit, the control unit operatively connected to an insertion mechanism configured to accept the disposed used sharp objects, wherein the sensing mechanism is configured to detect a threshold condition corresponding to a level of accumulation of disposed sharp objects within the container; wherein the insertion mechanism is suspended from an underside of the lid and extending into the interior space, configured to receive a sharp object for disposal and facilitate delivery of the sharp object into the container, wherein the insertion mechanism further comprises a locking mechanism that engages when the threshold condition is detected, preventing further insertion of sharp objects; and an alert system comprising at least one of a visual alert and an auditory alert, the alert system configured to notify a user when the threshold condition is detected.

2. The sharp object disposal housing of claim 1, wherein the plurality of sidewalls includes a front housing and a back housing, each designed to be detachable from one another for enhanced accessibility and maintenance.

3. The sharp object disposal housing of claim 1, featuring a hinged lid that also functions as a door, providing secure and convenient access to the interior space.

4. The sharp object disposal housing of claim 1, where the front housing includes a touch screen display for operational control and monitoring.

5. The sharp object disposal housing of claim 1, wherein the sensing mechanism within the base accurately detects the load of sharp objects.

6. The sharp object disposal housing of claim 1, wherein the insertion mechanism is designed to tilt for disposing sharp objects onto the base and featuring a locking mechanism activated at maximum capacity.

7. The sharp object disposal housing of claim 1, including a speaker system integrated for auditory alerts or instructions.

8. The sharp object disposal housing of claim 1, where the interior space is optimized to accommodate a specific volume of sharp objects.

9. The sharp object disposal housing of claim 1, incorporating a removable mount on at least one of the sidewalls for flexible placement.

10. The sharp object disposal housing of claim 1, constructed from materials resistant to punctures and chemical corrosion.

11. The sharp object disposal housing of claim 2, wherein at least one of front housing and the back housing includes a transparent or mesh section for internal visibility.

12. The sharp object disposal housing of claim 1, featuring a non-slip surface on the base for stability.

13. The sharp object disposal housing of claim 1, wherein the insertion mechanism is adaptable for various types and sizes of sharp objects.

14. The sharp object disposal housing of claim 1, designed for ease of cleaning and maintenance.

15. The sharp object disposal housing of claim 1, adaptable for use in different medical settings.

16. The sharp object disposal housing of claim 1, featuring user-friendly interfaces for efficient operation.

17. The sharp object disposal housing of claim 1, including additional safety features including biometric locks as well as RFID tags.

18. A sharp object disposal system comprising:

a base, a lid, and a plurality of sidewalls defining an interior space for disposing used sharp objects, the plurality of side walls including a front housing and a back housing that are removable from each other;

a container positioned within the housing for accumulating the used sharp objects; and a sensing mechanism located within the base and in electronic communication with a control unit, the control unit operatively connected to a tray configured to accept the disposed used sharp objects, wherein the sensing mechanism is configured to detect a maximum load threshold of disposed sharp objects within the container; wherein the tray is suspended from an underside of the lid and extending into the interior space, configured to receive a sharp object for disposal and tilt to release the sharp object into the container, wherein the tray is operatively coupled to a locking mechanism that engages when the maximum load threshold is reached, the locking mechanism configured to prevent further tilting of the tray, thereby preventing further insertion of sharp objects.

19. A sharp object disposal system comprising:

a base, a lid, and a plurality of sidewalls defining an interior space for disposing used sharp objects, the plurality of side walls including a front housing and a back housing that are removable from each other, wherein the lid acts as a front facing door;

a container positioned within the housing for accumulating the used sharp objects and accessible through the front facing door;

a sensing mechanism located within the base and in electronic communication with a control unit, the control unit operatively connected to a tray configured to accept the disposed used sharp objects, wherein the sensing mechanism is configured to detect a maximum load threshold of disposed sharp objects within the container within the housing;

a touch screen display integrated into the front housing for real-time load information;

a speaker system in a lower assembly affixed to both the front housing and the back housing for auditory alerts at maximum load; and the tray is suspended from an underside of the lid and extending into the interior space, configured to receive a sharp object for disposal and tilt to release the sharp object into the container, wherein the tray is operatively coupled to a locking mechanism that engages when the maximum load threshold is reached, the locking mechanism configured to prevent further tilting of the tray, thereby preventing further insertion of sharp objects.

* * * * *